United States Patent [19]
Sharma et al.

[11] Patent Number: 4,804,548
[45] Date of Patent: * Feb. 14, 1989

[54] NOVEL SWEETENER DELIVERY SYSTEMS

[75] Inventors: Shri C. Sharma, Mendham; Robert K. Yang, Morris Plains; James J. Shaw, Morristown, all of N.J.

[73] Assignee: Warner-Lambert Company, Morris Plains, N.J.

[*] Notice: The portion of the term of this patent subsequent to Jun. 21, 2005 has been disclaimed.

[21] Appl. No.: 112,656

[22] Filed: Oct. 22, 1987

Related U.S. Application Data

[62] Division of Ser. No. 658,101, Oct. 5, 1984, Pat. No. 4,752,485.

[51] Int. Cl.$^4$ .................... A23L 1/226; A23L 1/236
[52] U.S. Cl. .................................. 426/96; 426/99; 426/285; 426/548; 426/453; 426/650
[58] Field of Search .............................. 426/3-6, 426/548, 658, 453, 96, 99, 658, 305, 307, 650, 651

[56] References Cited

U.S. PATENT DOCUMENTS

| | | | |
|---|---|---|---|
| 2,064,727 | 12/1936 | Buer | 424/38 |
| 2,902,407 | 9/1959 | Gross | 424/38 |
| 3,080,292 | 3/1963 | Koff | 424/38 |
| 3,247,065 | 4/1966 | Koff | 426/72 |
| 3,362,829 | 6/1968 | Fujita et al. | 426/99 |
| 3,389,000 | 6/1968 | Toyonaka et al. | 426/307 |
| 3,443,959 | 5/1969 | Ciboit | 426/453 |
| 3,527,647 | 9/1970 | Hager | 426/453 |
| 3,647,480 | 3/1972 | Cermak | 426/99 |
| 3,753,739 | 8/1973 | Cella et al. | 426/548 |
| 3,780,170 | 12/1973 | Goodhart | 424/35 |
| 3,843,778 | 10/1974 | Diamond | 424/38 |
| 3,867,556 | 2/1975 | Darragh | 426/98 |
| 3,928,633 | 12/1975 | Shoaf et al. | 426/96 |
| 3,949,094 | 4/1976 | Johnson | 426/99 |
| 3,956,507 | 5/1976 | Shoaf et al. | 426/96 |
| 3,960,757 | 6/1976 | Morishita | 252/316 |
| 3,976,794 | 8/1976 | Johnson et al. | 426/103 |
| 4,001,456 | 1/1977 | Glicksman et al. | 426/548 |
| 4,059,706 | 11/1977 | Pischke et al. | 426/548 |
| 4,105,801 | 8/1978 | Degliotti | 426/99 |
| 4,122,195 | 10/1978 | Bahoshy et al. | 426/5 |
| 4,139,639 | 2/1979 | Bahoshy et al. | 426/3 |
| 4,293,572 | 10/1981 | Silva et al. | 426/307 |
| 4,374,858 | 2/1983 | Glass et al. | 426/5 |
| 4,380,534 | 4/1983 | Fukui | 424/38 |
| 4,382,924 | 5/1983 | Berling | 424/180 |
| 4,384,004 | 5/1983 | Cea et al. | 426/3 |
| 4,465,694 | 8/1984 | Okada | 426/3 |

FOREIGN PATENT DOCUMENTS

| | | |
|---|---|---|
| 0010320 | 4/1980 | European Pat. Off. . |
| 0177368 | 4/1986 | European Pat. Off. . |
| 0190826 | 8/1986 | European Pat. Off. . |
| 1900124 | 9/1969 | Fed. Rep. of Germany . |
| 2425764 | 1/1975 | Fed. Rep. of Germany . |
| 0967610 | 8/1964 | United Kingdom . |
| 1262556 | 2/1972 | United Kingdom . |
| 1446352 | 8/1976 | United Kingdom . |
| 1566609 | 5/1980 | United Kingdom . |
| 1573487 | 8/1980 | United Kingdom . |

Primary Examiner—Jeanette Hunter
Attorney, Agent, or Firm—Daniel A. Scola, Jr.; Gary M. Nath; Charles A. Gaglia, Jr.

[57] ABSTRACT

The present inventive compositions concern a stable delivery system capable of effecting a controlled release of core material comprising:

(A) at least one natural or artificial core material selected from the group consisting of amino acid based sweeteners, dipeptide sweeteners, glycyrrhizin, saccharin and its salts, acesulfame salts, cyclamates, steviosides, talin, dihydrochalcone compounds, drugs, medicaments, flavoring agents and mixtures thereof; and (B) a hydrophobic matrix consisting essentially of
  (i) lecithin; and
  (ii) an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and
  (iii) at least one glyceride.

6 Claims, 2 Drawing Sheets

NOVEL SWEETENER DELIVERY SYSTEMS

This is a divisional of copending application Ser. No. 658,101 filed on Oct. 5, 1984 now U.S. Pat. No. 4,752,485.

The present invention relates to a novel delivery system and method of preparation. More particularly this invention relates to a method of protecting materials from being adversely affected from such factors as moisture, pH, temperature and reactive chemicals. The delivery system is most useful for core materials such as sweeteners which are particularly unstable in the presence of these factors. In particular, the delivery system is especially useful for dipeptide sweeteners such as aspartame which are known to present stability problems, drugs, mdeicaments, flavoring agents and the like.

Dipeptide sweeteners such as L- aspartyl-L-phenylalanine methylester (aspartame) have been widely recognized as an extremely good-tasting non-caloric sweetener for use in a variety of food products, among which are chewing gum products. Unfortunately, aspartame is extremely unstable in the presence of moisture and undergoes hydrolytic degradation and subsequent loss of sweeteners. Elevated temperatures and specific ranges may accelerate the hydrolytic degradation. Additionally, aspartame is known to react with a number of flavors and chemicals such as aldehydes and ketones. For example, aspartame loses its sweetness due to chemical reactions in the presence of flavor aldehydecontaining oils such as cinnamon. These flavor oils are used in food products and are popular in chewing gum compositions and other confectionery products. Chewing gum compositions and other products also generally contain moisture and may be exposed to elevated temperatures during shelf-life. The result is the loss of aspartame and the corresponding loss of sweetness in the product.

Numerous attempts have been made to stabilize aspartame in chewing gums as well as other food products. U.S. Pat. No. 4,384,004 to T. Cea et al., discloses solid particles of aspartame encapsulated by a coating material selected from the group consisting of cellulose, cellulose derivatives, arabinogalactin, gum arabic, polyolefins, waxes, vinyl polymers, gelatin, zein and mixtures thereof, wherein the amount of said coating material to said methyl ester is from 1:1 to 1:10. More particularly, the coating materials include cellulose, methyl cellulose, ethyl cellulose, cellulose nitrate, cellulose acetate phthalate, carboxymethyl cellulose, hydroxyethyl cellulose, hydroxypropyl cellulose, arabinogalactan; polyethylene, polymethacrylates, polyamides, ethylenevinyl acetate copolymers, polyvinylpyrrolidone; gum arabic; paraffin wax, carnauba wax, spermaceti, beeswax; stearic acid, stearyl alcohol, glyceryl stearate; gelatin, zein and mixtures thereof.

The method of coating employed in this reference involves suspending the aspartame particles in a stream of air that passes through a zone of atomized liquid droplets of the coating material, so that the coating material is deposited on the surface of the aspartame. More than one coating may be used whereby the inner coating is water-soluble and the outer coating is water-insoluble.

U.S. Pat. Nos. 4,122,195 and 4,139,939, both to Bahoshy et al., fix aspartame by preparting it with a material such as gum arabic or the reaction product of a compound containing a polyvalent metallic ion, with an ungelatinized starch acid-ester of a substituted dicarboxylic acid, by a spray drying technique, where the aspartame and a film former are prepared in an emulsion.

U.S. Pat. No. 4,374,858, to Glass et al., discloses an aspartame sweetened chewing gum having improved sweetness stability wherein the chewing gum piece has aspartame coated on its surface, as opposed to incorporating it in the chewing gum mix.

EPA No. 81110320.0, published June 16, 1982 (Publication No. 0053844), to Ajinomoto Co., Inc., discloses a stabilized dipeptide-based sweetening composition comprising (a) from 20 to 60% by weight of solid fat, (b) from 10 to 30% by weight emulsifier, (c) from 10 to 30% by weight polysaccharide and (d) not more than 30% by weight of dipeptide sweetener. The compositions are prepared by heating the mixture of the ingredients, cooling, and pulverizing to obtain powder or granules of the composition to obtain a ASTM mesh size of smaller than 12. Spray drying the mixture is also disclosed.

U.S. Pat. No. 4,105,801 to Degliotti, discloses a confectionery comprising a core portion and a shell adheringly enveloping the core portion, whereby the shell is formed by an intimate mixture of microcrystals of xylitol with a solid fatty substance in a proportion of 0.5 to 15 parts by weight of fatty substance to each 100 parts by weight of xylitol. The fatty substance is preferably a mono-, di- or triglyceride having a melting range of between 20° and 60° C.

U.S. Pat. No. 3,389,000 to Toyonaka el al., discloses protective coatings for granular nucleoside-5-phosphates, the coatings being edible fats melting between 40°-100° C. and derived from plants and animals. Hydrogenated oils such as soybean oil, cottonseed oil, almond oil, castor oil, linseed oil, mustard oil, olive oil, grapefruit seed oil, palm oil, palm kernel oil, rapeseed oil, rice bran oil and the like and mixtures thereof. This reference discloses a process of preparing the granular product from a liquid mixture of fats and nucleoside-5-phosphates are sprayed from a pressure nozzle and the resultant granules cooled and recovered.

U.S. Pat. No. 4,382,924, to Berling, discloses liquid oral dosage forms for vitamins or pharmaceutical materials comprising an edible oil, a high potency lipid soluble sweetener such as saccharin and a lipid soluble flavorant. The edible oil may be a polyol fatty acid ester having at least four fatty acid ester groups and each fatty acid having from about 8 to about 22 carbon atoms. The oil, sweetener and flavor oil are mixed and heated and then cooled to provide a palatable liquid dosage form.

U.S. Pat. Nos. 3,949,094 and 3,976,494 both to Johnson, and U.S. Pat. No. 3,867,556 to Darragh present a general discussion of spraying fatty materials onto sweeteners and the like. U.S. Pat. No. 4,293,572 to Silva et al., discloses the application of a dispersion of an emulsified fat with a solution of dextrin, saccharin or a polysaccharide to a food product as a barrier against moisture. U.S. Pat. No. 3,527,647 discloses a process of agglomerating particles by randomly scattering and spraying moistened particles to cause them to collide and form agglomerates.

The problem relating to stabilization of sweeteners such as aspartame, which has not been previously addressed, relates to the wettability of the aspartame crystal as well as to its morphological configuration. Aspartame is known to be rodlike, elongated, needlelike or dendritic in shape. As a result it is very difficult to coat in ordinary mixing or spray coating techniques. To be effective as protective barriers coatings must be able to adhere to the crystalline surface, including the needle-like tips and other shape variations of the aspartame. Additionally, the coating must be capable of being applied in a film with a uniform thickness sufficient to provide a barrier against degradative factors such as moisture, pH changes, temperature changes and reactive chemicals. The coatings, in addition to being protective barriers, must be flexible enough to conform to the surface irregularities and geometrical configuration without cracking due to mechanical stresses which is is subjected to during incorporation of the sweetener into specific product applications. Attempts to coat aspartame using spray techniques to apply simple mixtures of fat and lecithin have resulted in poor wetting, spotty coating and inadequate protection against moisture and other potentially degradative factors.

It has been discovered, that simple mixing of known coating materials such as fats, with certain other core materials such as aspartame does not provide adequate protection to keep the core material in a stabilized state. Fats do not provide adequate coating onto aspartame, nor do such coating materials as starch, and certain other materials such as waxes. Many of these materials require solvents and moisture for application, which have adverse effects on the stability of hydrophilic instable materials such as aspartame. For example, simple mixing of aspartame in liquid mixtures of traditional coating materials, e.g., fat and lecithin has resulted in poor wetting, spotty coating and inadequate protection against moisture and chemicals. The result was degradation of the aspartame upon exposure to these conditions. Changes in pH and temperature catalyze these degradative conditions.

The process of EPA 81110320.9 (Publication No. 0053844) filed December 10, 1981, is an example of simple admixing of coating materials with aspartame. This publication discloses the simple melting and admixing of from 20 to 60% of solid fat, 10 to 30% of emulsifier, 10 to 30% of polysaccharide and not more than 30% of dipeptide sweetener. The mixture is then cooled and pulverized or spray dried. The pulverizing into fine powder, however, results in rupturing of the coating, leaving the aspartame exposed. Spray drying is normally associated with the driving off of moisture or solvents.

The prior art techniques for coating difficult to coat materials such as aspartame, has focused on two methods. The first method involves forming a molten mixture of the coating material with the sweetener. The mixture is then cooled and pulverized. The resultant particles represent a random attempt at completely coating or enrobing the sweetener. In the case of aspartame, this coating is not adequate protection against moisture or aldehyde-containing flavor oils and instability of the aspartame results.

The second conventional prior art technique for coating materials involves fluidized bed spray coating. This technique involves conducting a stream of the material to be coated into a zone of atomized droplets of coating material. In the case of materials such as aspartame, this method is very difficult. Aspartame is a low density material, has a large surface-to-weight ratio, and poor wetting characteristics. For these reasons, spray coating of aspartame in a fluidized bed system is difficult.

The instant process is an improvement over spray congealing techniques and includes additional coating steps. The resultant product exhibits a marked improvement in the effectiveness of the coating as a protective barrier. The result is a significant improvement in the stability of the core material. The examples discussed below, along with the microphotographs, clearly indicate that the instant process enables a uniform and thorough coating to be applied to a core material in complete contrast to the prior art techniques.

Thus, the delivery systems of the invention and process of preparation provide an improved protective coating for core materials. The delivery systems have a variety of other advantages including the controlled release of materials such as sweeteners, flavoring agents and medicaments and the masking of bitter taste for additional additives such as pharmaceutical compounds. Other advantages will become apparent herein.

FIG. I is a picture of the crystalline sweetener aspartame (magnification 145×). The rod-like geometry is clearly visible.

FIG. II is a picture of the agglomerate of aspartame and the hydrophobic matrix prior to application of the secondary coating. The spherical like appearance is clearly seen.

The agglomerate was formed using the inventive spray congealing technique. The shape of the agglomerate facilitates the secondary exterior coating applied via the fluidized bed granulation technique.

FIG. III is a picture of the inventive sweetener delivery system. (magnification 145×). These particles are the result of coating the agglomerate of FIG. II with 200% by weight of the agglomerate of a mixture of 95% hydrogenated palm oil and 15% paraffin wax.

FIG. IV is a picture of the sweetener delivery system (magnification 145×) as prepared by the method outlined in Example one EPA No. 81110320.9. The polysaccharide, however, was omitted and amounts of the ingredients were in the range of the instant invention. The method involved melting the ingredients of fat, lecithin aspartame and monoglyceride together and solidifying them by cooling. The solid was then pulverized to give the particles depicted in the photograph. As clearly seen in this picture, the particles are randomly and non-uniformly coated.

SUMMARY OF THE INVENTION

Although this invention contemplates a delivery system for a variety of core materials and combinations thereof, it is particularly directed to providing a novel delivery system for sweeteners such as aspartame and saccharin, drugs, medicaments, flavoring agents and the like. The inventive compositions and method of preparation solve the problems associated with wetting the surface of core materials. It particularly solves the problem of wetting the surface and thoroughly coating the needle-like structure of the dipeptide sweetener aspartame. Additionally, the coatings are flexible enough to form protective film barriers without cracking due to mechanical forces encountered during application of the coating to the core material as well as those mechanical stresses present when incorporating the delivery system into food products. The present method of stabilizing and coating the core material involves an initial formation of an agglomerate of the core material in a hydrophobic coating matrix whereby the core material is agglomerated and oriented in the matrix to facilitate a further coating or coatings with similar or the same matrix materials. The agglomerate is formed using spray congealing techniques which create an approximate eliptical or spherical shape. The agglomerate is, of course, larger in size then the individual particles, and its shape and size, as well as the composition of the matrix coating facilitate the application of the second coating. The agglomerate is screened to obtain only the desired particle size range. Agglomerates which are extremely fine, e.g., below about 200 U.S. standard mesh, are generally not useful since they are too fine to easily coat. The second coating and any additional coatings are applied using standard fluidized bed granulation techniques well known to the skilled artisan. Additionally, the inventive method involves spray congealing techniques without first forming an agglomerate. As discussed further, the spray congealing process involves feeding a molten mixture of the core material in the novel hydrophobic coating matrix of this invention through a high pressure spray nozzle, while maintaining the feed-line at a controlled temperature and adjusting the nozzle pressure to control the particle size of the spray. The resultant product takes the form of fine spherical droplets which congeal and solidify as they leave the nozzle and contact the air to form solid particles. These particles overcome the major problems associated with aspartame particles; that is, the needle-like shape is changed into a round aggregate matrix; the particle density is increased to a favorable range; and wettability is improved allowing granulation coating techniques to be effective. These particles comprise the delivery system discussed further herein.

The inventive delivery systems and compositions are useful in food products such as chewing gums, and other confectionery products, baked goods, pharmaceutical preparations, beverages, tobacco and proprietary products such as toothpaste and mouthwash. Acceptable amounts may vary widely and preferably from about 0.01% to about 100% by weight of the delivery system based on the weight of the final product.

DETAILED DESCRIPTION OF THE INVENTION AND PREFERRED EMBODIMENTS

The present inventive compositions concern a stable delivery system capable of effecting a controlled release of core material comprising:

(A) at least one natural or artificial core material selected fromt he group consisting of amino acid based sweeteners, dipeptide sweeteners, glycyrrhizin, saccharin and its salts, acesulfame salts, cyclamates, steviosides, talin, dihyrochalcone compounds, drugs, medicaments, flavoring agents and mixtures thereof; and (B) a hydrophobic matrix consisting essentially of
  (i) lecithin; and
  (ii) an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and
  (iii) at least one glyceride.

Lecithin is critical to the hydrophobic matrix and is believed to serve several important purposes. Most importantly, lecithin acts as a wetting agent to increase the affinity of the fat or wax to the core material surface. Fat and wax are ordinarily not compatible with certain crystalline sweeteners such as aspartame. The lecithin mediates the poor affinity between these materials and allows for uniform wetting of the aspartame surface by the fat or wax. Uniform wetting of the surface is critical to proper adherence of the hydrophobic matrix coating and to the effectiveness of the ultimate protection it provides for the core material.

Secondly, lecithin serves as a modifier of the rheological and thermal properties of the fat which lends it the capability of forming an elastic (non-brittle) and flexible film over a wider temperature range. Ordinary fat without lecithin would result in a brittle, porous crystalline coating which would be vulnerable to rupture during processing and which would fail to uniformly wet the core material surface. Additionally, lecithin acts to modify the morphological properties of the fat or wax, as well as to increase their heat capacity, thereby retarding liquid to solid phase transitions and allowing for increased flexibility in processing conditions, e.g., the mixture can be processed in a specified temperature range for a longer period of time. The increased heat capacity plays an important role in the final delivery system since more heat will be required before the system melts down and releases the core material. Thus, at short exposures to elevated temperatures, the delivery system will be more stable than without the addition of lecithin.

The high bulk density and high surface area to weight ratio of core materials such as aspartame make them generally difficult to coat. Lecithin increases the viscosity of the fat which facilitates their incorporation.

The *Condensed Chemical Dictionary,* 9th edition, Van Nostrand Reinhold, 1977, defines lecithin as mixtures of diglycerides of fatty acids linked to the choline ester of phosphoric acid. Lecithins are classed as phosphoglycerides or phosphatides. In the instant invention, the lecithin preferably has a minimum of about 95% by weight of phosphatide present. This purity level is generally designated in commercially available lecithins as "95% acetone insolubles." The phrase "95% acetone insolubles" is intended to mean that upon dissolution of the lecithin in acetone, 95% of the lecithin (the phosphatide portion) remains insoluble. Residual impurities such as oil, moisture and soluble non-phosphatides account for the 5% of the materials dissolved and extracted by the acetone. More preferably, the lecithin employed will have 97% insolubles. Additionally, it is required that the lecithin be soluble in the fatty acid or wax. This is necessary for the lecithin to perform its various functions described above. The lecithin employed does not have a defined melting point range but softens prior to decomposition.

The second required constituent in the hydrophobic matrix coating of the delivery system is an edible material which is itself hydrophobic and which has a melting point in the range of about 25° C. to about 100° C. Those materials useful are selected from the group consisting of fatty acids, natural, synthetic waxes and mixtures thereof. It is important that the melting point be within the recited range since the melting point of the final delivery system product will be greatly affected by the fat or wax constituent.

Those fatty acids which are useful must have an iodine value of about 1 to about 10. The iodine value is a means of determining the degree of unsaturation in fats and oils. The measurement of iodine values are determined by known titrating methods and are reported in terms of centrigrams of iodine absorbed per gram of fat and oil sample. (See *Bailey's Industrial Oil and Fat Prod-* ucts, Vol 2, 4th Ed., Swern, Daniel ed., p 436–438, 1982). Thus, those fatty acids useful in the inventive systems have an iodine value of about 1 centrigram to about 10 centrigrams.

Examples of the fatty acids employed are selected from the froup consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil and mixtures thereof.

Those waxes which are useful include natural waxes such as animal waxes, vegetable waxes, petroleum waxes and synthetic waxes having a melting point within the range of about 25° C. to about 100° C. and being edible. Specific examples of waxes which fall within these categories are beeswax, lanolin, bayberry, sugar cane, candelilla, carnauba, paraffin, microcrystalline, petrolatum and carbowax. Mixtures of these waxes may be used as well as mixtures of the waxes with the fatty acids.

The edible fatty acid or wax materials are employed in the instant delivery systems in amounts of about 61% to about 95% by weight of the delivery system, preferably in amounts of about 63% to about 90% and most preferably in amounts of about 66% to about 80%. These amounts are necessary to adequately coat the surface of sweeteners such as aspartame which have a high surface area to weight ratio. Hydrogenated palm oil is the most preferred fatty acid. Paraffin wax and mirocrystalline wax are the preferred waxes.

The edible fatty acid or wax component is critical to the effectiveness of the protective barrier. The hydrophobic matrix, of which the fatty acid or wax is an essential part, provides protection for the core material from heat, light, moisture, pH, reactive chemicals and the like. Additionally, the release of the core material is controlled via the hydrophobic matrix and can serve other purposes such as the masking of taste for unpalatable or unpleasant tasting materials.

The term glyceride component used herein refers to commonly identified glycerides which are esters of glycerol and fatty acids in which one or more of the hydroxyl groups of the glycerol have been replaced by acid radicals. Mono- and diglycerides are preferred, whereas triglycerides alone are not acceptable.

The mono- or diglyceride component of the hydrophobic coating matrix serves to increase the affinity between the fatty acid or wax and the core material. In addition, for core materials which are water soluble such as aspartame, the mono- or diglyceride component also serves to help the fat adhere and wet to the sweetener surface. Flexibility and elasticity of the matrix once it forms the film or coating on the core material is increased due to the glyceride component.

The dlycerides are present in amounts of about 0.5 to about 20% by weight of the delivery system. Preferably the glyceride is used in amounts of about 0.5 to about 7% and most preferably about 1% to about 3%. It should be recognized that mixtures of mono- and diglycerides may be used, since most available glyceride materials are mixtures of mono- and diglycerides.

The core material can be selected from a wide variety of materials such as sweeteners, medicaments, drugs, flavoring agents and the like. These materials can be used either singly or in combination in either a single or multiple delivery system. That is, one or more of these materials may be present within one coating matrix or separately coated by the matrix and employed alone or in combination in a final product.

The sweetener component may be selected from solid natural or synthetic sweeteners capable of imparting high intensity sweetness. These sweeteners are selected from the group consisting of amino acid based sweeteners, dipeptide sweeteners, glycyrrhizin, saccharin and its salts, acesulfame salts, cyclamates, steviosides, talin, dihydrochalcone compounds and mixtures thereof.

The sweeteners may be used in amounts necessary to impart sweetness and preferably in amounts of about 0.01 to about 30% by weight of the delivery system. Aspartame, saccharin and its salts are the preferred sweeteners and may be used in amounts of about 0.01% to about 25% and about 0.01% to 50% respectively, by weight of the delivery system. The preferred amounts of these sweeteners are about 2 to about 10%, most preferably 4 to about 6%.

A particularly effective combination of sweeteners is aspartame, sodium saccharin and acesulfame K (potassium acesulfame). Saccharin and its salts and acesulfame salts may be employed in amounts of about 5 to about 50% by weight. Aspartame is used in amounts up to about 15% by weight when used in this combination. One or more of the sweeteners may be in the encapsulated form prior to incorporation in the delivery system, thus delaying the release of the sweetener and lengthening the perceptible sweetness and/or staggering their release. Thus, the sweeteners may be incorporated such that they release sequentially.

It has also been discovered that the incorporation of the combination of two or more sweeteners used, alone or in the delivery system improves the sweetness intensity and prolongs the sweetness release. This sweetness improvement is the result of synergism. Exemplary examples of synergistic combinations are: saccharin/aspartame; saccharin/potassium acesulfame; saccharin/aspartame/ potassium acesulfame. These sweeteners can also be added to the final food product independently of the delivery system. Thus, a food product may have sweetness imparted thereto attributable to the delivery system sweetness as well as those sweetners independent of the delivery system. These combinations of sweeteners have also been discovered to impart a long lasting flavor effect to the food product such as chewing gum.

The medicament drugs used herein may be selected from a wide variety of drugs and their acid addition salts. Both organic and inorganic salts may be used provided the drug maintains its medicament value and is provided the drug maintains its medicament value and is soluble in the solvent. Exemplary acid salts include hydrochloride, hydrobromide, orthophosphate, benzoate, maleate, tartrate, succinate, citrate, salicylate, sulfate, and acetate.

The weight percent of the drug or its acid addition salt thereof, based on the weight of the coating matrix preferably from about 1% to about 20%, and most preferably about 5% to about 15%, which amounts will vary depending upon the therapeutic dosage permitted.

Suitable categories of drugs that may be employed in the instant composite may vary widely and generally represent any stable drug combination. Illustrative categories and specific examples include:
 (a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, and phenyltoloxamine citrate, (c) Decongestants, such as phenylphrine hydrochloride, phenylpropanolamine hydrochloride, pseudoephedrine, hydrochloride ephedrine; and (d) Various alkaloids, such as codeine phosphate, codeine sulfate and morphine.

(e) Mineral supplements such as potassium chloride and calcium carbonates.

These materials may be used alone or in combination within the ranges specified above.

These flavoring agents may be chosen from synthetic flavoring liquids and/or liquids derived from plants, leaves, flowers, fruits and so forth, and combinations thereof. Representative flavoring liquids include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit and fruit essences including apple, strawberry, cherry, pineapple and so forth.

The amount of flavoring agent employed is normally a matter of preference subject to such factors as flavor type, base type and strength desired. In general, amounts of about 0.05% to about 3.0% by weight of the final chewing gum composition are usable with amounts of about 0.3% to about 1.5% being preferred and about 0.7% to about 1.2% being most preferred.

The method of preparing the delivery system involves first forming an agglomeration of the core material and the hydrophobic matrix. The agglomerates are then screened to obtain particles of about 200 to about 30 mesh and then coated with one or more layers of hydrophobic material to provide a protective barrier. The agglomerate is formed by mixing at low shear the fatty acid or wax with the glyceride and lecithin at temperatures of about 75° to about 95° C. until a homogeneous mixture is obtained. The core material or combination of core materials are then added to this mixture and mixed at high shear to uniformly dispense the material in the mixture. The dispersion is then fed into a heat controlled spray nozzle and spray congealed. The term spray congealed as used herein refers to the solidification of the atomized liquid droplets which cool and solidify upon hitting the cooler temperature of the surrounding atmosphere. The nozzle pressure is regulated to control the particle droplet size. The droplets cool and congeal once they are emitted from the nozzle and contact the cooler environment. The result is a dry particle or agglomerate having an approximate eliptical or spherical shape. At this stage, core material particles are bound together with the hydrophobic matrix, but not adequately coated to fully protect the core material from the environment. The agglomerated particles are then screened to the desired size as mentioned above. The second coating step of the process is now necessary to provide the required protective barrier. Thus, the agglomerate is then coated using standard fluidized bed granulation procedures.

The second coating (e.g., the coating of the agglomerate) may use the hydrophobic matrix. It should be mentioned, however, that the outer coating need not have the lecithin and glyceride components present since wetting of the core material surface is not critical at this point, having been accomplished in the first coating. Thus, the outer coating need only have the fatty acid and wax component and preferably both. Preferably the outer coating comprises hydrogenated palm oil and paraffin wax in respective amounts of about 61% to about 90% and about 10% to about 40%. The final product is a fine dry particle and is referred to herein as the delivery system. The delivery system preferably has a melting range of about 20° C. to about 90° C. and most preferably a melting range of about 35° to about 38° C., such that it melts and releases the core material within the normal body temperature range of humans.

As an alternative, but less preferred method, the homogeneous mixture of the hydrophobic matrix and core material can be allowed to cool in sheets and subsequently pulverized to a particle size of about 30 to about 200 U.S. standard mesh size (about 600 to about 75 microns.) The pulverized particles can then be coated with the hydrophobic mixture using standard fluidized bed granulation techniques. An additional alternative method of forming the delivery system comprises spray drying the core material with a known binder such as cellulose or polyvinyl pyrrolidone and the like to form an aggregate. The aggregate is then coated with the hydrophobic coating matrix using conventional fluidized bed granulation techniques well known to the skilled artisan. These alternative methods however are not as effective in preparing the delivery systems as the preferred method.

It is important to note that the preferred inventive process involving spray congealing of the liquid hydrophobic coating matrix-core material followed by fluidized bed granulation results in a significantly and surprisingly improved coating for protection of the core material. Either spray congealing or fluidized bed granulation alone do not provide adequate protective coatings for the delivery system and results in instability and results in premature release of the core material. The congealing step forms an agglomerate of the core material and hydrophobic matrix. The matrix binds together the core particles but only partially coats the core. The core material is "randomly" coated in the sense that is is pure chance that the matrix completely coats or enrobes the material particularly if the material is difficult to coat.

Figure 1:
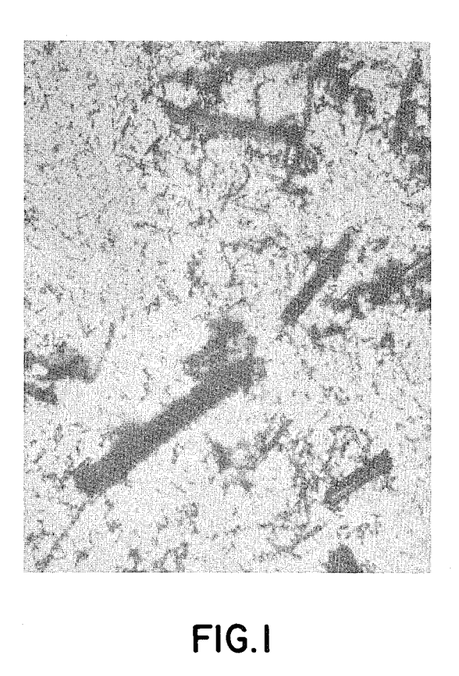
Figure 2:
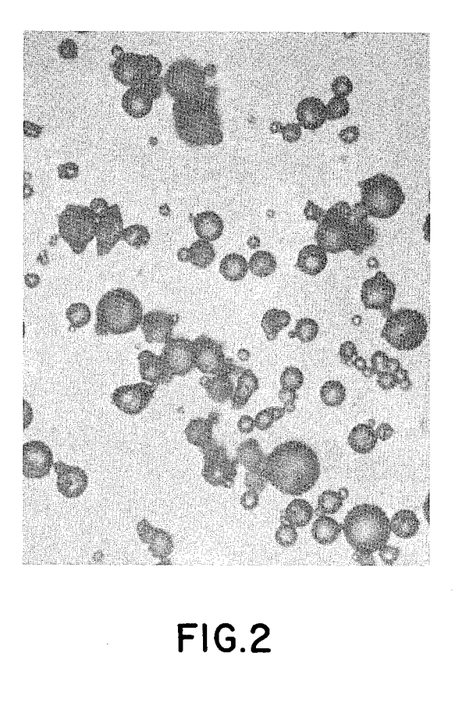
Figure 3:
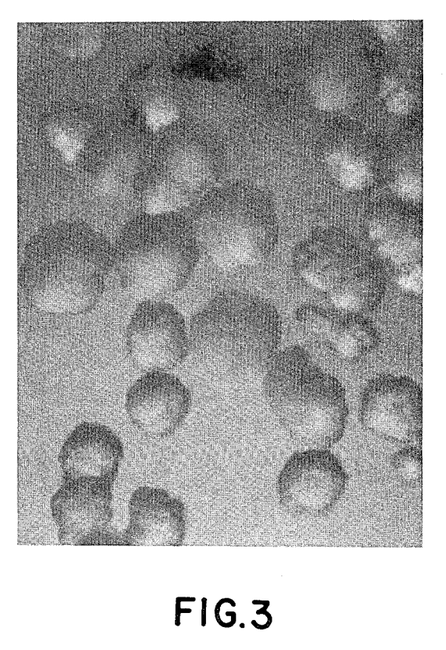
Figure 4:
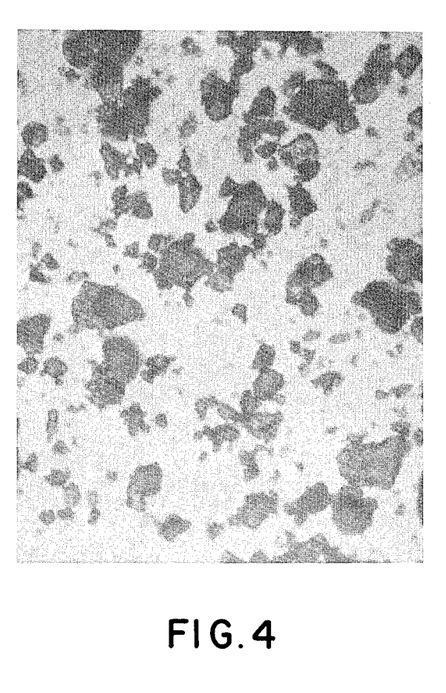

Fluidized bed granulation is necessary to achieve the uniform coating necessary to protect the core material. For example, with rod-like or needle-like shaped sweeneners such as aspartame, the spray congealing orients the aspartame crystals into and agglomeration which is significantly easier to coat, e.g., the agglomerate approximates an eliptical or spherical shape (see FIG. 2), which is then easily uniformly coated in the fluidized bed. Fluidized bed coating alone of sweeteners such as aspartame does not provide a uniform protective coating.

The effectiveness of the protective barrier or coating afforded by the hydrophobic matrix to the core material is dependent not only on the completeness of the surface area coated, but also on the thickness of the coating. The external hydrophobic matrix thickness is approximated as a function of the total amount of hydrophobic matrix present as follows:

| Coating* | Thickness** | Dissolution*** |
|---|---|---|
| 300% | 29 | N.D. (not detectable) |
| 200% | 22 | N.D. |
| 100% | 13 | N.D. |
| 50% | 7 | 0.3% |

-continued

| Coating* | Thickness** | Dissolution*** |
|----------|-------------|----------------|
| 30%      | 3           | 7.57%          |
| 0%       | 0           | 17.64          |

*percentage of outer coating of hydrophobic matrix by weight of the intermediate agglomerate.
**indicates the relative thickness of the outer coating over the agglomerate as a percentage of the diameter of the agglomerate itself.
***delivery system placed in water at 25° C. for 1 hour. Percentage indicates the amount of aspartame extracted by water.

As evidenced in the above table, the thickness of the exterior, secondary coating (e.g., the fluidized bed coating of the agglomerate) is greater when a higher weight percentage of coating is used. The thicker coating maximizes the protection of the core material, in this case aspartame.

A balance must be maintained, however, such that too thick a coating is not used so as to prevent proper release of the core material. It has been determined that using the exterior coating in amounts of about 200 to about 300% by weight of the agglomerate maximizes the protective benefits with the controlled release benefits. Use of the exterior coating in less than amounts of about 30% by weight of the agglomerate does not provide thickness sufficient for protection of the core material. As evidenced by teh table above, the less coating used the lower the coating thickness and the higher the dissolution of the core material (sweetener) from the delivery system, as indicated by the dissolution data. These data were determined by stirring a specified amount of the delivery system in water at 25° C. for 1 hour. The amount of core material (sweetener) dissolved by the water was then measured and used as an indicator of the effectiveness of the coating as a moisture barrier. As the data values indicate, no sweetener (aspartame) was detectable in the water where the coating was greater than 200% by weight of the agglomerate. This indicates the coating thickness and uniformity was extremely effective in preventing moisture from penetrating and reacting with the aspartame. Coatings which were 30% or less by weight of the agglomerate showed significant percentages of aspartame detected by the dissolution assay, indicating penetration of the water through the coating. When no coating was used on the agglomerate, significant dissolution of the aspartame occurred.

The delivery system in its final form is a dry spherical particulate having a U.S. standard mesh size of about 200 to about 30 and preferably about 150 to about 70.

The delivery system can be used to protect materials such as sweeteners, drugs, medicaments, flavoring agents, and the like. The delivery systems provide an excellent means of masking unpleasant tasting drugs such as potassium chloride and the like, making consumption of the drug more appealing to the public.

The delivery system in its final form may be referred to as a composite. The composite is useful in a variety of foot products medicaments, baked goods, pharmaceutical preparations, tobacco and proprietary products such as toothpaste and mouthwash, and the like. Once prepared the composite may be stored for future use or formulated with conventional additives, that is, pharmaceutically acceptable carriers and confectionery ingredients to prepare compositions which offer a variety of textures to suit particular applications. Such compositions may be in the form of a lozenge, stored for future use or formulated with conventional additives, that is pharmaceutically acceptable carriers and confectionery ingredients to prepare compositions which offer a variety of textures to suit particular applications. Such compositions may be in the form of a lozenge, tablet, toffee, nougat, chewy candy, chewing gum, and so forth. The pharmaceutically acceptable carriers may be selected from a wide range of materials. Without being limited thereto, such materials include diluents, binders and adhesives, lubricants, disintegrants, colorants, flavorings, sweeteners and miscellaneous materials such as buffers and adsorbents in order to prepare a particular medicated composition. The preparation of confectionery and chewing gum products is historically well known and has changed very little over the years.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added. In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc.

By comparison, the high boiling syrup, or "bob syrup", is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY:* Science and Technology, 2nd edition, AVI Publishing Co., Inc., Westport, Connecticut, (1980), at Pages 424–425.

Pharmaceutical tablets of this invention may also be in the form of chewable forms. This form is particularly advantageous because of convenience and patient acceptance and rapid onset of bioactivity. To achieve acceptable stability and quality as well as good taste and mouth feel several considerations are important, namely amount of active substance per tablet, flavor, compressibility and organoleptic properties of the drug.

The preparation of chewable medicated candy is prepared by procedures similar to those used to make soft confectionary. This procedure generally involves the formation of a boiled sugar-corn syrup blend to which is added a frappe mixture. The boiled sugar-corn syrup blend may be prepared from sugar and corn syrup blended in parts by weight ratio of 90 to 10 : 10 to 90. This blend is heated to temperatures above 250° F. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 150° F. and 250° F. The composite can then be added as the temperature of the mix is lowered below the melting point of the matrix whereupon additional ingredients are added such as flavors, and colorants. The formulation is further cooled and formed to pieces of desired dimensions.

A general discussion of the lozenge and chewable tablet forms of confectionery may be found in H.A. Lieberman and L. Lachman, *Pharmaceutical Dosage Forms: Tablets* Volume 1, Marcel Dekker, Inc., New York, N.Y. at pages 289 to 466.

With regard to the chewing gum formulation in which the novel delivery system may be employed, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of α-pinene or β-pinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminium silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list: sugars such as sucrose, glucose (corn syrup), dextrose, invert sugar, fructose, and mixtures thereof; saccharine and its various salts such as the sodium or calcium salt; cyclamic acid and its various salts such as the sodium salt; the dipeptide sweeteners such as aspartame; dihydrochalcone; glycyrrhizin; *Stevia rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Reissue patent 26,959. Also contemplated is the synthetic sweetener 3,6-dihydro-6-methyl-1-1,2,3-oxathiazin-4-one-2,2-dioxide particularly the potassium (Acesulfame-K), sodium and calcium salts thereof as described in German Pat. No. 2,001,017.7.

Suitable flavorings include both natural and artificial flavors, and mints such as peppermint, methanol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition weight.

The colorants useful in the present invention, include the pigments such as titanium dioxide, that may be incorporated in amounts of up to about 1% by weight, and preferably up to about .6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Voluem 5, at Pages 857–884, which text is accordingly incorporated herein by reference.

The following examples serve to provide further appreciation of the invention but are not meant in any way to restrict the effective scope of the invention. All percentages throughout the specification are by weight % of the final delivery system unless otherwise indicated.

EXAMPLE ONE

This example demonstrates the preferred composition and method of preparation. A mixture of 333.3 grams of hydrogenated palm oil, and 41.7 grams of monoglyceride were melted at a temperature of about 85° C. To this mixture 41.7 grams of lecithin was added and mixed until it dissolved. At this point the mixture is homogeneous. Next 83.3 grams of aspartame is added and mixed at high shear to obtain a uniform dispersion of the sweetener. The molten mixture is then fed into a heat controlled high pressure nozzle and sprayed under controlled pressure to obtain a particle droplet size of about 160 to about 30 U.S. standard mesh. Particles outside this size range were screened out. The droplets congealed upon contact with the cooler atmosphere, forming a dry powder material. This powder is the agglomerate referred to herein. The agglomerate is then coated with a molten mixture of 1275 grams of hydrogenated palm oil and 225 grams of paraffin wax using standard fluidized bed granulation techniques. A Glatt GPC-15 fluidized bed granulator is used. The inlet temperature of the molten mixture is about 55° to about 65° C. and the outlet temperature is about 35° to about 40° C. The rate of spray is about 80 milliliters per minute at a pressure of about 3 bar. The spray is directed into a stream of aspartame suspended in an apparatus that creates a strong upward air current in which the sweetener moves. The stream of aspartame passes through a zone of the finely atomized droplets of the molten coating material, after which the thus coated particles pass out of the upward stream and pass downward in a fluidized condition counter current to the flow of heated fluidized gas whereupon they are dried, and may re-enter the upward moving coating zone for a subsequent discrete coating application. The foregoing method and associated apparatus are known as the Wurster Process. This process is set forth in detail in U.S. Pat. Nos. 3,089,824; 3,117,027, 3196,827, 3,241,520 and 3,253,944.

The resultant sweetener delivery system is a dry powder.

EXAMPLE TWO

The inventive sweetener delivery system was formed using the procedure of Example One whereby 300 grams of rapeseed oil, 30 grams of the monoglyceride, 50 grams of lecithin and 40 grams of aspartame was used. The agglomerate was formed in the same manner as Example one and then coated using the fluidized bed technique with a molten mixture of 400 grams of hydrogenated palm oil and 100 grams of paraffin wax.

EXAMPLE THREE

The procedure of Example two was repeated using the same amounts for making the agglomerate. The secondary fluidized bed coating, however, was carried out using the molten mixture of 380 grams of rapeseed oil and 120 grams of microcrystalline wax.

EXAMPLE FOUR

By way of comparison, the procedure of EPA No. 81110320.9 referred to above, was carried out omitting the polysaccharide component in order to properly compare it with the inventive process. A molten mixture of 120 grams of hydrogenated palm oil, 20 grams of monoglyceride, 20 grams of lecithin and 30 grams of aspartame was prepared in accordance with the procedures of Example One of the reference. The mixture was cooled to obtain a solidified mass and then pulverized to obtain the final encapsulated product.

The product was then photographed under a microscope 145X and presented in FIG. IV. As the photograph clearly shows the irregular and random nature of the coating. This is to be compared with the results of the spray congealing-fluidized bed process of applicants as shown in the FIG. III photograph. FIG. III clearly depicts spherical-like uniform coatings of the instant invention having the agglomerate coated with 200% of the secondary coating by weight of the aggregate.

EXAMPLE FIVE

The procedure of Example One was repeated using the same ingredients and amounts only 83 grams of saccharin was used to replace the aspartame.

EXAMPLE SIX

The procedure of Example One was repeated using the same ingredients except the sweetener comprised 12.5 grams of aspartame and 70.5 grams of saccharin.

EXAMPLE SEVEN

This example demonstrates an alternative method of preparing the inventive delivery systems. A mixture of 100 grams of hydrogenated palm oil, 30 grams of lecithin, 30 grams of monoglyceride and 25 grams of aspartame were mixed allowed to cool and solidify. The resultant solid was then ground to a mesh of about 30 to about 80. The ground particles were then placed in a fluidized bed granulator as in Example one and coated with a mixture comprising 425 grams of hydrogenated palm oil and 75 grams of paraffin wax. The resultant product was the dry powdered sweetener delivery system.

EXAMPLE EIGHT

This example demonstrates another alternative method of forming the inventive sweetener delivery systems. In this method 1.5 Kg of aspartame is first granulated in a fluidized bed of aspartame is first using 300 ml of 5% methylcellulose in an ethanol-water (50:50) solution. This process results in the formation of larger granules of aspartame which are then dried and passed through a 20 mesh sieve to remove any large lumps. The resulting particles are then coated in the fluidized bed with a mixture comprising 6.8 Kg hydrogenated palm oil, 1.7 kg paraffin wax, 1.5 Kg lecithin and 1.5 Kg monoglyceride.

EXAMPLE NINE

This example demonstrates an attempt to coat aspartame with lecithin. The mixture of 95 grams of lecithin and 5 grams of aspartame was melted and cooled. The mixture was cooled, solidified and ground to a particle size of about 30 mesh.

EXAMPLE TEN

The delivery systems of Examples 1–4 and 6–9 were subjected to a dissolution study intended to test the resistance of the coatings to water. The delivery systems of each example were placed in individual beakers of water at 25° C. for one hour while stirring. The water was then assayed for detection of aspartame and the results, shown below, clearly demonsrtate the inventive delivery systems (Examples 1-3 and 7 in particular) afford more resistance against moisture than the prior art (Examples 4 and 9). This is indicated by the fact that no aspartame was detected in the water of the preferred inventive examples, while 12.88% and 79.89% aspartame was found in the water of the prior art examples.

Example 8, a less preferred alternative method of the instant invention showed a slight dissolution of aspartame in the water.

TABLE I

Dissolution study: delivery system in agitated water for 1 hour at 25° C.

| Delivery System | % Aspartame found in water by weight of delivery system |
|---|---|
| Example One (inventive) | N.D.* |
| Example Two (inventive) | N.D. |
| Example Three (inventive) | N.D. |
| Example Four (Comparative Process) | 12.88% |
| Example Seven (inventive) | N.D. |
| Example Eight | 2.53% |
| Example Nine (comparative coating) | 79.89% |

*N.D. indicates "none detectible"

EXAMPLE ELEVEN

This example is intended to demonstrate the criticality of lecithin to the sweetener delivery systems. An aggregate of aspartame is formed by mixing 1.1 Kg of aspartame with 300 ml of 5% methylcelulose ethanol-water (50:50) solution. The solution is then sprayed in a fluidized bed granulator as discussed in previous examples to obtain dry aggregates of aspartame. The aggregates are passed through a 30 mesh sieve to obtain the desired particle size. The aggregated particles are then coated using the previously discussed fluidized bed method with a mixture of 1 Kg of monoglyceride, 6 Kg hydrogenated palm oil. A dissolution study as discussed in Example Ten was run with the result of 8.14% aspartame being detected in the water. This indicates that the hydrophobic matrix had not properly wet and adhered to the surface of the aspartame crystals and the coating therefore, had not sufficiently adhered to provide an adequate moisture barrier.

EXAMPLE TWELVE

This example demonstrates the use of the mineral supplement potassium chloride as the core material in the inventive delivery system. The process of Example One was used. The resulting product had a pleasing mouth-feel and did not exhibit the typical astringent and bitter taste of the KCl salt.

The delivery system contained the following ingredients and amounts: Delivery System

| Ingredient | Amount |
|---|---|
| Monoglyceride | about 0.5 to about 30% |
| Hydrogenated Palm Oil | about 61 to about 80% |
| Lecithin | about 0.5 to about 20% |
| Potassium Chloride* | about 10 to about 20% |
| Sweetener | about 5 to about 15% |

*KCl is pre-ground through a 60 mesh sieve.

EXAMPLE THIRTEEN

Example twelve was repreated substituting about 5% to about 15% (200 mesh) of chlorostryramine in place of KCl.

EXAMPLE FOURTEEN

Example twelve was repeated using about 4 to about 10% pseudoephedrine HCl in place of KCl. The resulting delivery system did not exhibit the typical bitter and astringent taste of the drug.

EXAMPLE FIFTEEN

Example twelve was repeated substituting about 4 to about 10% dextromethorphan for the KCl. The resulting delivery system did not exhibit the bitter and astringent taste of the drug.

EXAMPLE SIXTEEN

This example uses a flavor oil as the core material for the delivery system. Peppermint oil in the amount of about 5% to about 20% was added to the delivery system of Example One in place of the sweetener component.

The invention being thus described, it will be obvious that the same may be varied in many ways. Such variations are not to be regarded as a departure from the spirit and scope of the invention and all such modifications are intended to be included within the scope of the following claims.

What is claimed is:

1. A composite sweetener and flavoring delivery system having a substantialy hydrophobic exterior comprising
   (A) an agglomerated mixture of a core material selected from the group consisting of sweeteners, flavoring agents and mixtures thereof and a matrix wherein the matrix comprises:
      (i) about 0.5% to about 20% fat soluble lecithin;
      (ii) about 61% to about 90% of an edible material having a melting point in the range of about 25° C. to about 100° C. selected from the group consisting of (a) a fatty acid having an iodine value of about 1 to about 10; (b) natural waxes; (c) synthetic waxes; (d) and mixtures thereof;
      (iii) about 0.5% to about 20% of a glyceride; said composite having a melting point in the range of about 20° C. to about 90° C.

2. The composite of claim 1 wherein the sweetener is an artificial sweetener selected from the group consisting of amino acid based sweeteners, dipeptide sweeteners, saccharin and salts thereof, acesulfame salts, cyclamates, steviosides, dihydrochalcone compounds, talin, glycyrrhizin and mixtures thereof.

3. The sweetener composite of claim 2 wherein the sweetener si aspartame present in the amount of about 0.01% to about 25%.

4. The composite of claim 2 wherein the sweetener is saccharin and its salts present in amounts of about 0.05 to about 50% by weight.

5. The composite of claim 2 wherein the sweetener is a combination of up to about 15% aspartame, about 5% to about 50% saccharin and its salts and about 5% to about 50% potassium acesulfame.

6. The composite of claim 1 wherein the fatty acid is selected from the group consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil and mixtures thereof.

* * * * *